United States Patent
Thomas et al.

(10) Patent No.: US 12,319,295 B2
(45) Date of Patent: Jun. 3, 2025

(54) APPARATUS AND METHOD FOR DETERMINING A COGNITIVE STATE OF A USER OF A VEHICLE

(71) Applicant: JAGUAR LAND ROVER LIMITED, Coventry (GB)

(72) Inventors: Philip Thomas, Coventry (GB); David Rumbold, Coventry (GB); Ersin Kurnaz, Coventry (GB); Fahad Qasim, Coventry (GB)

(73) Assignee: JAGUAR LAND ROVER LIMITED, Coventry (GB)

( * ) Notice: Subject to any disclaimer, the term of this patent is extended or adjusted under 35 U.S.C. 154(b) by 273 days.

(21) Appl. No.: 17/756,109

(22) PCT Filed: Nov. 17, 2020

(86) PCT No.: PCT/EP2020/082367
§ 371 (c)(1),
(2) Date: May 17, 2022

(87) PCT Pub. No.: WO2021/099302
PCT Pub. Date: May 27, 2021

(65) Prior Publication Data
US 2022/0402500 A1   Dec. 22, 2022

(30) Foreign Application Priority Data
Nov. 18, 2019   (GB) ........................... 1916746

(51) Int. Cl.
*B60W 40/08* (2012.01)
*A61B 5/01* (2006.01)
(Continued)

(52) U.S. Cl.
CPC ............... *B60W 40/08* (2013.01); *A61B 5/01* (2013.01); *A61B 5/163* (2017.08); *A61B 5/18* (2013.01);
(Continued)

(58) Field of Classification Search
CPC ............... B60W 40/08; B60W 50/085; B60W 2040/0872; B60W 2540/221;
(Continued)

(56) References Cited

U.S. PATENT DOCUMENTS

| 9,977,593 B2 * | 5/2018 | Ricci ........................ G07C 5/08 |
| 2006/0149428 A1 * | 7/2006 | Kim ..................... B60W 40/09 701/1 |

(Continued)

FOREIGN PATENT DOCUMENTS

GB        2528083 A        1/2016

OTHER PUBLICATIONS

Great Britain Intellectual Property Office, Combined Search and Examination Report under Sections 17 and 18(3) Issued in Application No. GB1916746.9, Aug. 17, 2020, 11 pages.
(Continued)

*Primary Examiner* — Frederick M Brushaber
(74) *Attorney, Agent, or Firm* — McCoy Russell LLP

(57) ABSTRACT

The system comprises input means for receiving user data from associated user monitoring means that each monitor at least one respective attribute of the user of the vehicle. The user data is indicative of the plurality of respective attributes. A plurality of inference modules each receive user data from the user monitoring means, and each determine a respective inference of a cognitive state of the user based on the received user data. Each inference module is arranged to output user state data indicative of the determined inference of the cognitive state of the user. An inference fusion module
(Continued)

receives the user state data from each of the plurality of inference modules to determine an inference of an aggregated cognitive state of the user and to output cognitive state data indicative of the aggregated cognitive state for controlling the vehicle functions.

19 Claims, 8 Drawing Sheets

(51) Int. Cl.
*A61B 5/16* (2006.01)
*A61B 5/18* (2006.01)
*B60W 50/08* (2020.01)

(52) U.S. Cl.
CPC ... *B60W 50/085* (2013.01); *B60W 2040/0872* (2013.01); *B60W 2540/221* (2020.02); *B60W 2540/225* (2020.02)

(58) Field of Classification Search
CPC ... B60W 2540/225; B60W 2050/0075; B60W 2420/403; B60W 2556/10; B60W 50/06; B60W 2050/0088; B60W 2540/22; B60W 2540/229; A61B 5/01; A61B 5/163; A61B 5/18

See application file for complete search history.

(56) References Cited

U.S. PATENT DOCUMENTS

| | | | |
|---|---|---|---|
| 2007/0182529 A1* | 8/2007 | Dobler | B60W 40/08 340/438 |
| 2014/0135598 A1* | 5/2014 | Weidl | A61B 5/48 600/300 |
| 2018/0222493 A1* | 8/2018 | Singh | B60W 50/14 |

OTHER PUBLICATIONS

ISA European Patent Office, International Search Report and Written Opinion Issued in Application No. PCT/EP2020/082367, Jan. 25, 2021, WIPO, 14 pages.

* cited by examiner

APPARATUS AND METHOD FOR DETERMINING A COGNITIVE STATE OF A USER OF A VEHICLE

CROSS REFERENCE TO RELATED APPLICATIONS

The present application is a U.S. National Phase of International Application No. PCT/EP2020/082367 entitled "APPARATUS AND METHOD FOR DETERMINING A COGNITIVE STATE OF A USER OF A VEHICLE," and filed on Nov. 17, 2020. International Application No. PCT/EP2020/082367 claims priority to Great Britain Patent Application No. 1916746.9 filed on Nov. 18, 2019. The entire contents of each of the above-listed applications are hereby incorporated by reference for all purposes.

TECHNICAL FIELD

Aspects of the disclosure relate to a system, to a vehicle, to a method, and to computer software. Aspects of the present disclosure relate to determining a cognitive state of a user of a vehicle.

BACKGROUND

It is increasingly desired to provide more intelligent vehicle functionality to remove, or reduce, a need for a user of a vehicle to manually control functionality of the vehicle. For example, it is desired to reduce a need for a user of a vehicle to manually control an interior environment, such as temperature, or an interior of a vehicle. In this way the user is provided with a more relaxing journey, particularly in a vehicle having at least partly autonomous functionality, and to allow a user to concentrate on driving a vehicle when in charge of the vehicle.

It is an object of embodiments of the disclosure to at least mitigate one or more of the problems of the prior art.

SUMMARY

According to aspects of the present disclosure, there is provided a driver assistance system, a vehicle, and a method and computer software.

According to an aspect of the present disclosure there is provided a system for determining a cognitive state of a user of a vehicle to control one or more function of the vehicle, the system comprising input means for receiving user data indicative of a plurality of attributes of the user, a plurality of inference modules each arranged to receive user data and determine an inference of a cognitive state of the user, and an inference fusion module arranged to determine an aggregated cognitive state of the user in dependence on each of the inferred cognitive states.

Advantageously, inferring an aggregated cognitive state of the user enables the driver assistance system to learn user preferences and control vehicle functions to improve the cognitive state of the user.

According to an aspect of the present disclosure there is provided a system for determining a cognitive state of a user of a vehicle to control one or more functions of the vehicle, the system being implemented by one or more controllers, the system comprising: input means for receiving user data from a plurality of associated user monitoring means for each monitoring at least one respective attribute of the user of the vehicle, the user data being indicative of the plurality of respective attributes; a plurality of inference modules each arranged to receive user data from one or more of the user monitoring means, and to each determine a respective inference of a cognitive state of the user in dependence on the received user data, wherein each of the plurality of inference modules is arranged to output user state data indicative of the determined inference of the cognitive state of the user; and an inference fusion module arranged to receive the user state data from each of the plurality of inference modules, to determine an inference of an aggregated cognitive state of the user and to output cognitive state data indicative of the aggregated cognitive state for controlling the one or more functions of the vehicle in dependence thereon.

Optionally, the one or more controllers may collectively comprise: at least one electronic processor having an electrical input for receiving the user data; and at least one memory device electrically coupled to the at least one electronic processor and having instructions stored therein; and wherein the at least one electronic processor is configured to access the at least one memory device and execute the instructions thereon so as to realise the plurality of inference modules and the inference fusion module.

Optionally, the input means are arranged to receive the user data indicative of one or more of biometric, physical and psychological attributes of the user. For example, the input means may be arranged to receive one or more of ECG data, heart rate data, temperature data or facial expression data. The user data may be indicative of one or more of biometric, physical and psychological attributes of the user when the user was away from the vehicle.

The input means may be optionally arranged to receive context data indicative of a context of the user. The context data may comprise user context data relating to when the user was away from the vehicle. The context of the user may comprise an indication of one or more previous locations of the user or one or more travel modes of the user.

Optionally one or more of the inference modules may comprise: a threshold monitor arranged to receive the user data and to determine, in dependence on the user data and at least one threshold values, an active state of the user; and an active time monitor arranged to receive an indication of the active state from the threshold monitor and to determine, in dependence on a temporal threshold value, the inference of the cognitive state of the user.

Each of the plurality of inference modules may be optionally arranged to output a wrapper including user state data indicative of the determined inference of the cognitive state of the user at a plurality of points in time.

Optionally the inference fusion module may be arranged to determine a primary cognitive state and a secondary cognitive state of the user in dependence on the received user state data.

The inference fusion module is optionally arranged to determine the cognitive state of the user in dependence on the received user state data and one or more baseline parameters associated with the user indicative of a dormant state of the user. The inference fusion module may be arranged to update the baseline parameters associated with the user in dependence on the user data.

Optionally, the inference fusion module is arranged to determine the cognitive state of the user in dependence on the received user state data and learned inference information associated with the user, wherein the learned inference information associates user data with one or more cognitive states.

Optionally, the inference fusion module is arranged to determine the cognitive state of the user comprising selecting from amongst a plurality of predetermined cognitive states.

The inference fusion module may comprise relative baseline offset, RBO, information. The inference fusion module may be arranged to process the user data in dependence on the RBO information to remove an offset from the user data.

Optionally, the system may comprise an input means for receiving context data indicative of a context of one or both of the user and the vehicle; an input means for receiving preference data indicative of one or more preferences associated with the user, where the preferences associate one or more of the cognitive states of the user with one or more settings of at least one vehicle system; processing means for controlling the one or more functions of the vehicle in dependence on the cognitive state data, the context data and the preference data; and output means for outputting control data for controlling the one of more functions of the vehicle. The processing means may be arranged to receive further cognitive state data responsive to the control of the one or more vehicle functions. The processing means may be arranged to update the preference data indicative of a correlation between the cognitive state and the control of the one of more functions of the vehicle.

Optionally, the input means is arranged to receive visual user data from a visual monitoring means for visually monitoring the user of the vehicle. The plurality of inference modules may comprise a visual inference module arranged to determine an inference of a visual state of the user in dependence on the visual user data. The visual state may be a state determinable from appearance, for example, bored, annoyed, tired. The visual inference module may be arranged to output visual state data indicative of the inference of the visual state of the user.

The visual user data may be facial expression data indicative of one or more attributes of a facial expression of the user, for example yawn, brow furrow, or eye closure.

Optionally, the visual inference module comprises a plurality of visual state monitoring units, wherein each monitoring unit is arranged to identify a respective visual state of the user.

Optionally, the input means may comprise an input means for receiving biometric user data from a biometric monitoring means for monitoring one or more biometric attributes of the user of the vehicle. The plurality of inference modules may comprise a biometric inference module arranged determine an inference of a biometric state of the user in dependence on the biometric user data, and to output the user state data indicative of the inference of the biometric state of the user. Optionally, the biometric user data is indicative of one or more of a heart rate or skin conductance value of the user.

Optionally, the input means may comprise an input means for receiving thermal user data from a temperature monitoring means for monitoring a temperature of at least a portion of the user of the vehicle. The plurality of inference modules may comprise a thermal inference module arranged determine an inference of a thermal state of the user in dependence on the thermal user data, and to output thermal state data indicative of the inference of the thermal state of the user.

Optionally, the input means comprise an input means for receiving gaze data from a gaze monitoring means for monitoring the gaze of the user of the vehicle. The plurality of inference modules may comprise a gaze inference module arranged determine an inference of a gazing state of the user in dependence on the gaze data, and to output gaze state data indicative of the inference of the visual state of the user.

The plurality of input means may optionally comprise an input means for receiving contextual user data from a device associated with the user, wherein the contextual user data is indicative of a behaviour of the user prior to entering the vehicle.

According to an aspect of the present disclosure, there is provided a vehicle comprising a system as described above.

According to an aspect of the present disclosure, there is provided a method of determining a cognitive state of a user of a vehicle to control one or more functions of the vehicle, the method comprising: receiving user data from a plurality of associated user monitoring means for each monitoring at least one respective attribute of the user of the vehicle, the user data being indicative of the plurality of respective attributes; determining a plurality of inferences of a respective cognitive states of the user in dependence on the received user data; determining an inference of an aggregated cognitive state of the user indicative of the aggregated cognitive state for controlling the one or more functions of the vehicle in dependence thereon.

Optionally, the method may comprise receiving an indication of one or more threshold values; determining, in dependence on the user data and at least one threshold value, an active state of the user; and determining, in dependence on the active state and a temporal threshold value, the inference of the cognitive state of the user.

According to yet further aspect of the present disclosure, there is provided computer software which, when executed by a computer, is arranged to perform a method as described above. The computer software may be tangibly stored on a computer readable medium.

According to an aspect of the present disclosure, there is provided a system for controlling one or more functions of a vehicle responsive to a cognitive state of a vehicle user, the system being implemented by one or more controllers, the system comprising an input means configured to receive cognitive state data indicative of a cognitive state of the user of the vehicle, and context data indicative of a context of one or both of the user and the vehicle; processing means configured to determine control data for controlling the one or more functions of the vehicle in dependence on the received indication of the cognitive state of the user and the context data; and output means configured to output the control data for controlling the one of more functions of the vehicle.

Advantageously, this aspect of the disclosure enables functions of a vehicle to be controlled in dependence on a determined cognitive state of the user in a given context.

Optionally, the one or more controllers may collectively comprise: at least one electronic processor having an electrical input for receiving the cognitive state data and the context data; and at least one memory device electrically coupled to the at least one electronic processor and having instructions stored therein; and wherein the at least one electronic processor is configured to access the at least one memory device and execute the instructions thereon so as to determine the control data for controlling the one or more functions of the vehicle in dependence on the received indication of the cognitive state of the user and the context data.

Optionally, the input means may be configured to receive preference data indicative of one or more preferences associated with the user, where the preferences associate one or more of the cognitive states of the user with one or more settings of at least one vehicle system, and the processing means may be configured to determine the control data for controlling the one or more functions of the vehicle further in dependence on the preference data.

Optionally, the processing means may be arranged to receive further cognitive state data responsive to the control of the one or more vehicle functions and to update the preference data indicative of a correlation between the cognitive state and the control of the one of more functions of the vehicle. Advantageously, the preference data is updated to reflect the change in the user's cognitive state in response to the control of the one or more vehicle functions, thereby allowing the system to learn user setting preferences for a given context.

Optionally, the processing means is arranged to update the preference data indicative of a positive correlation between the further cognitive state and the control of the one of more functions of the vehicle.

Controlling the one or more vehicle functions may optionally comprises controlling one or more of: heating, ventilation or air-conditioning (HVAC) settings associated with the vehicle; settings associated with an audio environment within the vehicle; a navigation system of the vehicle; or settings associated with a powertrain or suspension system of the vehicle.

Optionally, the context data is indicative of an environment of the user in the vehicle. The environment of the vehicle may comprise one or more of a luminance, audible, thermal or physical environment.

Optionally, the context data is indicative of a status of the user in the vehicle. The status of the user may be indicative of one or more of an activity being undertaken by the user, and a location of the user within the vehicle.

Optionally, the cognitive state data is indicative of an attentiveness of the user to a current task.

According to an aspect of the present disclosure, there is provided a vehicle comprising a system as described above.

According to an aspect of the present disclosure, there is provided a method of controlling one or more functions of a vehicle responsive to a cognitive state of a vehicle user, comprising: receiving cognitive state data indicative of a cognitive state of the user of the vehicle; receiving context data indicative of a context of one or both of the user and the vehicle; determining control data for controlling the one or more functions of the vehicle in dependence on the received indication of the cognitive state of the user and the context data; and outputting the control data for controlling the one of more functions of the vehicle.

Optionally, the method comprises receiving preference data indicative of one or more preferences associated with the user, where the preferences associate one or more of the cognitive states of the user with one or more settings of at least one vehicle system, and determining the control data for controlling the one or more functions of the vehicle further in dependence on the preference data indicative of one or more preferences associated with the user.

Optionally, the method comprises receiving further cognitive state data responsive to the control of the one or more vehicle functions; and updating the preference data indicative of a correlation between the cognitive state and the control of the one of more functions of the vehicle.

Optionally, the method comprises updating the preference data indicative of a positive correlation between the further cognitive state and the control of the one of more functions of the vehicle.

Optionally, controlling the one or more vehicle functions comprises controlling one or more of: one or more heating, ventilation or air-conditioning (HVAC) settings associated with the vehicle; one or more settings associated with an audio environment within the vehicle; a navigation system of the vehicle; and one or more settings associated with a powertrain or suspension system of the vehicle.

The context data is optionally indicative of an environment of the user in the vehicle. The environment of the vehicle may comprise one or more of a luminance, audible, thermal or physical environment.

Optionally, the context data is indicative of a status of the user in the vehicle. The status of the user may be indicative of one or more of an activity being undertaken by the user, and a location of the user within the vehicle.

The cognitive state data is optionally indicative of an attentiveness of the user to a current task.

According to a yet further aspect of the present disclosure, there is provided computer software which, when executed by a computer, is arranged to perform a method as described above. The computer software may be tangibly stored on a computer readable medium.

According to a yet further aspect of the present disclosure, there is provided a non-transitory, computer-readable storage medium storing instructions thereon that, when executed by one or more electronic processors, causes the one or more electronic processors to carry out a method as described herein.

BRIEF DESCRIPTION OF THE DRAWINGS

Embodiments of the disclosure will now be described by way of example only, with reference to the accompanying figures, in which.

DETAILED DESCRIPTION

Embodiments of the present disclosure relate to determining an inference of a cognitive state of a user of a vehicle. The inference of the cognitive state of the user is indicative of the user's state of mind. For example, within a vehicle the user may be bored, stressed, too hot, annoyed by lighting within or entering the vehicle etc. Embodiments of the disclosure are arranged to infer the user's cognitive state.

Some embodiments of the disclosure control one or more features of the vehicle responsive to the inference of the cognitive state.

Figure 1:
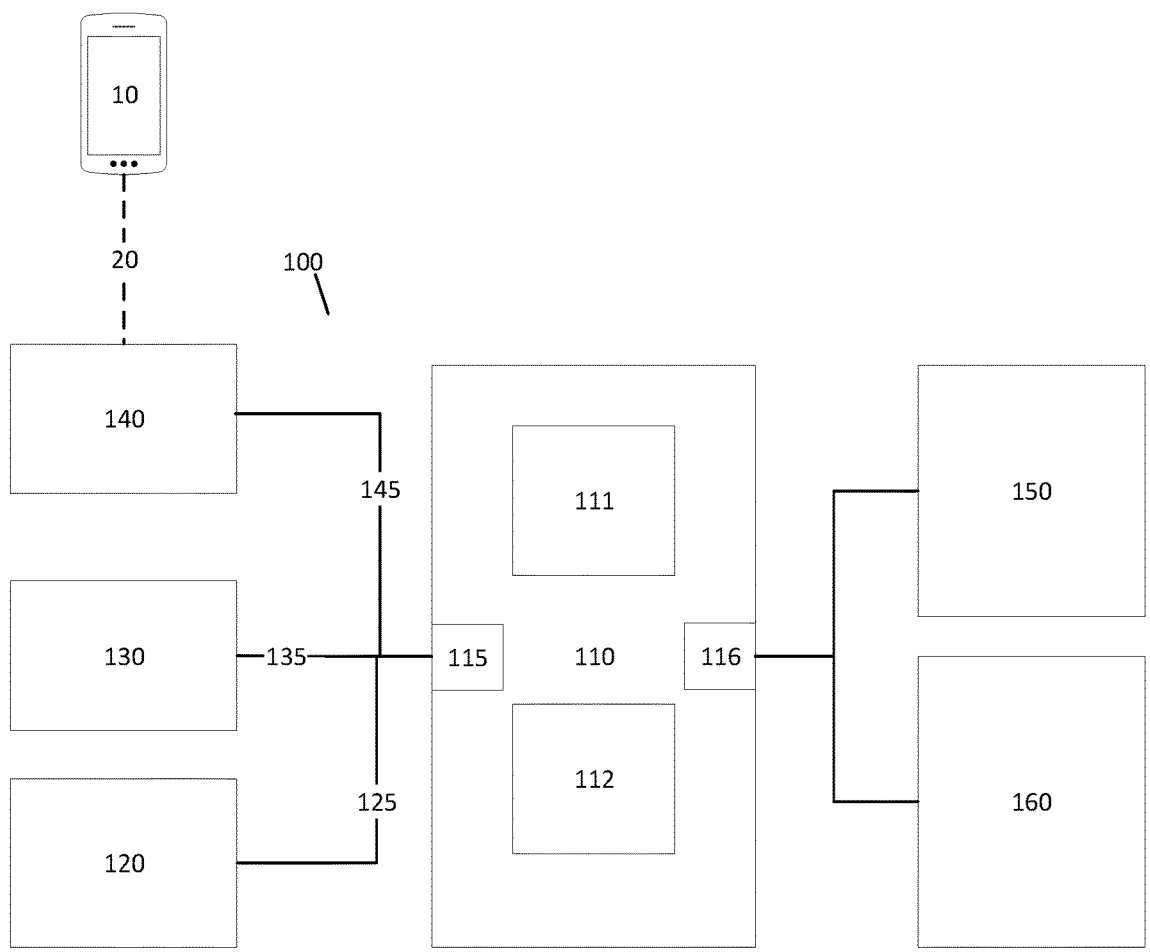
FIG. 1 shows a system according to an embodiment of the present disclosure.
Figure 2:
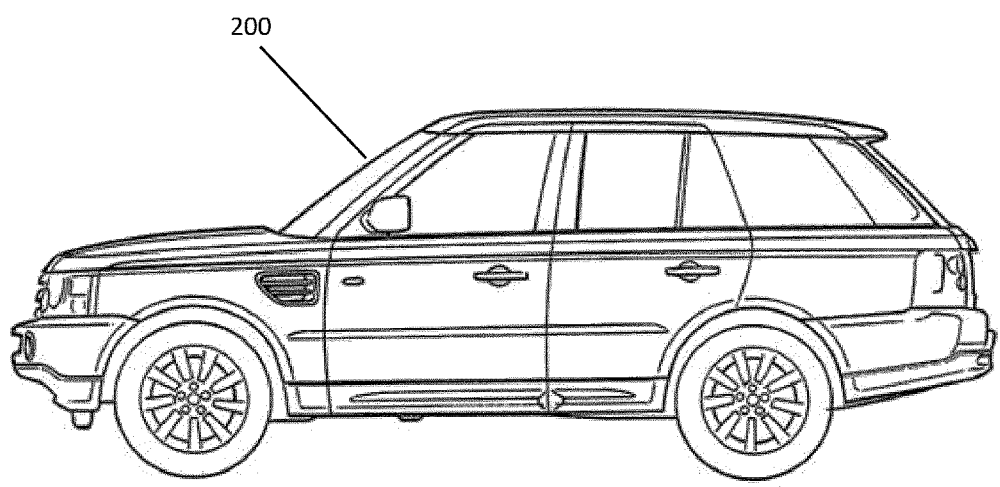
FIG. 2 shows a vehicle according to an embodiment of the present disclosure.

FIG. 1 illustrates a system 100 for determining a cognitive state of a user of a vehicle according to an embodiment of the disclosure. The system 100 determines the cognitive state of the user which may be used to control one or more functions of the vehicle, as will be explained. The system 100 may be implemented in a vehicle 200, such as a land-going or wheeled vehicle 200, as illustrated in FIG. 2. It will be appreciated that the system 100 may be used in other situations, such as within aircraft for example. In use, the system 200 may determine an inference of the cognitive state of an occupant of the vehicle 200 such as a driver of the vehicle 200 or an occupant responsible for control of the vehicle 200 in a case where the vehicle 200 is capable of at least partly autonomous operation or driving.

The cognitive state of the user is a state of mind of the occupant of the vehicle 200. The cognitive state may be selected from a plurality of predetermined cognitive states of the occupant, as will be explained.

The system 100 comprises one or more electrical controllers 110. Each electrical controller 110 may be operative to execute computer-readable instructions to, at least partly, perform a method according to an embodiment of the disclosure. The system 100 illustrated in FIG. 1 comprises one controller 110 with it being appreciated that this is merely illustrative.

The controller 110 comprises, in some embodiments, processing means in the form of one or more electronic processors 111. The one or more processors 111 may operatively execute computer-readable instructions which may be stored in a storage means 112 which may be in the form of one or more memory devices 112. The one or more memory devices 112 may store the computer readable instructions therein representing a method according to an embodiment of the disclosure as will be explained.

The controller 110 comprises an input means 115 to receive electrical signals. The input means 115 may be an electrical input to the controller 110. The electrical input 115 may be an interface to a communications network of the vehicle 200 such as communications bus which may be, for example, CANBus or an Ethernet based network although other protocols may be envisaged. The controller 110 further comprises an output means 116 for outputting electrical signals. The output means 116 may be an electrical output of the controller 110. The electrical output 116 may be an interface to the communications network of the vehicle 200. In some embodiments the input and output means 115, 116 may be integrated into a single IO means or interface to the network providing input and output of electrical signals in the form of data to the network.

The system 100 comprises user-monitoring means (UMM) 120 for determining one or more attributes associated with the user of the vehicle 200. The UMM 120 comprises one or more user-monitoring devices 120 arranged to monitor the user and to output user data 125 indicative of a respective one or more attributes of the user. The user-monitoring devices 120 may comprise at least some devices for monitoring physical attributes of the user, such as biometric, physical and psychological attributes of the user and outputting the user data 125 indicative thereof.

In some embodiments, the UMM 120 may comprise biometric monitoring means for monitoring one or more biometric attributes of the user of the vehicle 200. The biometric monitoring means may comprise one or more devices for measuring electrical attributes of the user, such as electrical activity of the user's body. For example, the system may comprise an electrocardiogram (ECG) device. The biometric monitoring means may comprise a heart monitoring device for determining a heart rate of the user or a skin monitoring device for determining a skin conductance value of the user. The UMM 120 may comprise a thermal monitoring means for monitoring one or more thermal attributes of the user and outputting the user data 125 indicative thereof. The thermal monitoring means 120 may comprise one or more thermal measurement device such as, for example, a long-wave infra-red (LWIR) camera although it will be appreciated that other devices may be used.

The UMM 120 may comprise one or more imaging means or imaging devices such as cameras for outputting the user data 125 indicative of one or more visual attributes of the user. The user data 125 indicative of the user may be image data indicative of an image of at least a portion of the user such as the user's face. The one or more imaging devices may comprise infra-red cameras which are better able to provide the user data in variable light conditions particularly low-light conditions.

The system 100 comprises, in some embodiments, vehicle monitoring means (VMM) 130 for determining one or more attributes associated with the vehicle 200 and outputting vehicle data 135 indicative thereof. The VMM 130 may comprise one or more sensing devices associated with the vehicle 200 for measuring respective attributes associated with the vehicle 200. The vehicle data 135 may be received at the controller 110 over the communications bus of the vehicle 200 from the sensing devices.

In some embodiments, the system 100 comprises a communications means 140 for communicating with a mobile device 10 associated with the user to provide user data 145 in the form of user context data 145 associated with the user. Often users are associated with one or more mobile devices 10, such as a mobile phone, tablet computer, smart watch, fitness tracker etc which may be carried by the user such as, in some cases, by being attached to the user's body, clothing or carried by the user e.g. in a bag or pocket. Such mobile devices 10 may be referred to as Internet of Things (IoT) sensors associated with the user. At least some of the mobile devices 10 are capable of determining a geographic location of the user when away from the vehicle 200 and may also determine movement data indicative of a travel mode of the user away from the vehicle, such as one or more of on foot, rail, tram, cycle etc. In this way, when the mobile device is wirelessly communicable, as indicated at 20 in FIG. 1, with the communication means 140, the context data 145 associated with the user is received from the mobile device 10 via the communication means 140. The wireless communication means may be a wireless communication module which supports a wireless communication protocol such as Bluetooth or WiFi although other communication protocols may be used. The protocol may be a short-range communication protocol e.g. less than 200 m, so that the mobile device 10 and communication module 140 are communicable when in proximity to receive the context data 145.

The context data 145 may be indicative of the user's behaviour away from the vehicle 200. The system 100 may store historic context data 145 received from the mobile device 10. In some embodiments, the system 100 is arranged to learn from received context data 145 about the user's behavioural patterns. For example, the system 100 may learn the user's work location based on the context data 145 being indicative of the user regularly spending working hours at a particular working location. When new context data 145 is received from the mobile device 10 the system 100 may infer the user's future behaviour in the vehicle 200. For example, if the context data 145 is indicative of the user having been at the working location, the system 100 may infer one or both of the user's destination and route to be taken in the vehicle to a home location.

The system 100 may comprise output means 150 for outputting information to the user. The output means 150 may be arranged to output information to the user visually, audibly or haptically. The output means 150 may comprise one or more output devices such as one or more visual display devices, one or more audio output devices and one or more haptic output devices.

In some embodiments the system 100 comprises one or more control means 160 for controlling one or more aspects of the vehicle 200. The control means 160 may be arranged to control, for example, an audiovisual system of the vehicle, such as to select audio to be provided within the vehicle 200, an environmental control system within the vehicle 200 which may comprise a heating/cooling or HVAC system of the vehicle 200, a navigation system of the vehicle 200 etc.

Figure 3:
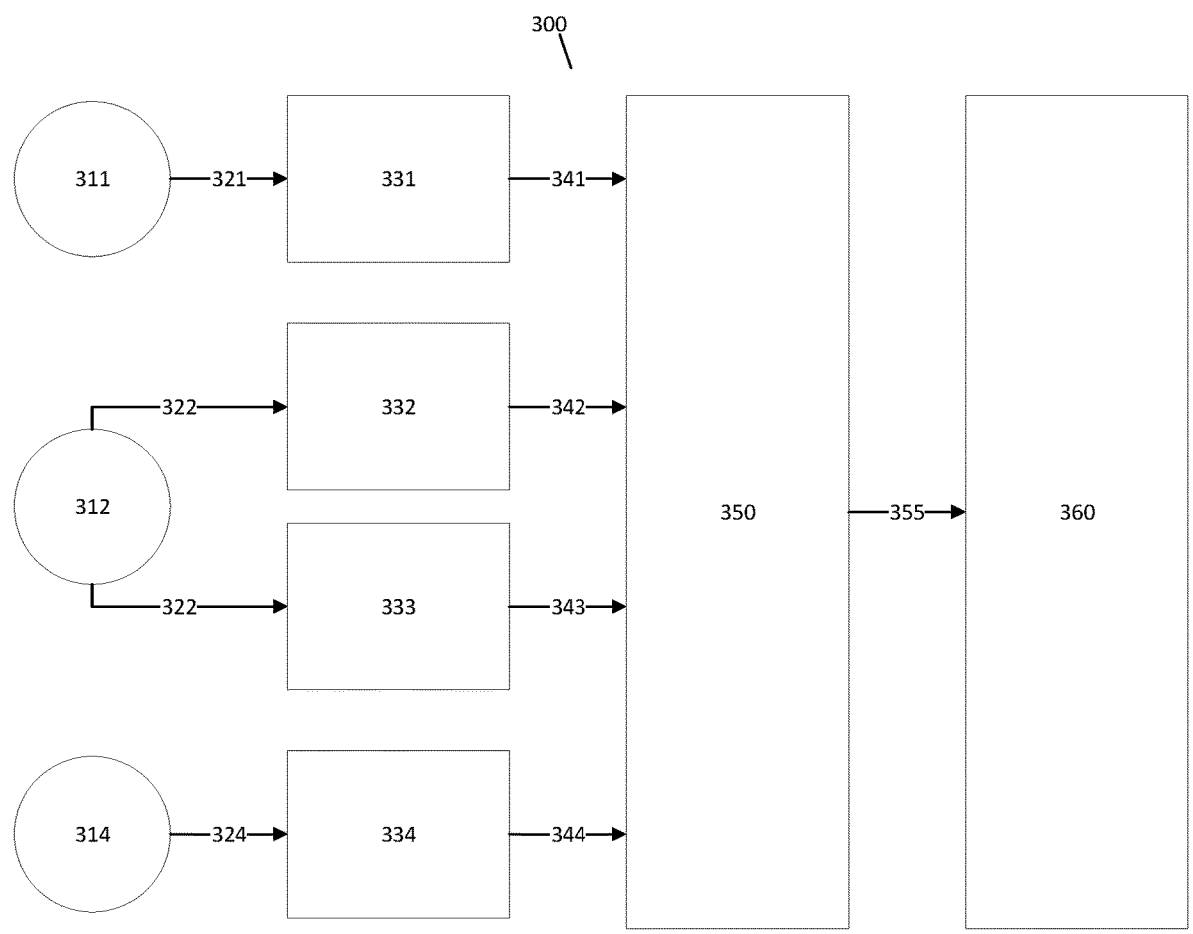
FIG. 3 shows a schematic illustration of a system according to an embodiment of the present disclosure.

Referring to FIG. 3, there is illustrated a system 300 according to an embodiment of the disclosure. The system 300 is a system for determining the inference of the cognitive state of a user of a vehicle, such as the vehicle 200 illustrated in FIG. 2. The system 300 is schematically illustrated in FIG. 3 and may be implemented by the system 100 described above with reference to FIG. 1. The system 300 comprises a plurality of modules 331-334, 350, 360, as will be explained, which may each be implemented by computer-readable software instructions stored on a computer readable medium, such as the one or more memory devices 112 of the system 100, and may be executed on the one or more electronic processors 111 of the system 100 to implement the system 300.

The system 300 illustrated in FIG. 3 comprises one or more UMMs 311, 312, 314, one or more inference modules 331, 332, 333, 334 associated with the UMMs 311, 312, 314 and an inference fusion module 350. In some embodiments, the system 300 further comprises a response engine 360 for controlling one or more functions of the vehicle 200. The UMMs 311, 312, 314 are arranged to output user data 321, 322, 324 indicative of respective attributes of the user of the vehicle 200 upon which the one or more inference modules 331, 332, 333, 334 determine inferences of the cognitive state of the user. The inference fusion module 350 is arranged to bring together, or combine, the inferences of the cognitive state of the user as will be explained. The inference fusion module 350 is arranged to output cognitive state data 355 as will be explained. The cognitive state data 360 is received by the response engine 360 for controlling one or more functions or aspects of the vehicle 200.

In the illustrated embodiment the system 300 comprises a plurality of UMMs 311, 312, 314 each arranged to monitor at least one respective attribute of the occupant of the vehicle 200. Each of the UMMs is arranged to output user data 321, 322, 324 indicative of the at least one respective attribute of the occupant.

In one example, a first UMM 311 is an electrocardiogram 311 for determining electrical activity of the occupant's heart. The electrocardiogram 311 may comprise one or more electrical contacts arranged within the vehicle 200 to contact the occupant's body to receive an electrical signal indicative of heart activity of the occupant. The electrocardiogram 311 is arranged to output first user data 321 indicative of the electrical activity which may be referred to as ECG data 321.

A second UMM 312 is a first imaging device 312, such as a camera arranged to operate within a first predetermined wavelength band. In one embodiment the first imaging device 312 is an infrared (IR) camera arranged to output image data indicative of a radiation in an infrared wavelength range, such as a short-wavelength IR wavelength of 0.9-1.7 μm emitted from the occupant. The first imaging device 312 is arranged to output second user data 322 which may be in the form of IR image data 322. As shown in FIG. 3, the IR image data may be provided to a plurality of inference modules 332, 333 of the system 300. That is, a plurality of inference modules may receive the same data and be configured to each determine a respective, different, attribute of the occupant.

A third UMM 314 is a second imaging device 314, such as a camera arranged to operate within a second predetermined wavelength band. In one embodiment the second imaging device 314 is an long-wave infrared (LWIR) camera arranged to output image data indicative of a radiation in a long-wave infrared wavelength range, such as around 7-14, or 8-14 μm, emitted from the occupant. The second imaging device 314 is arranged to output third user data 324 which may be in the form of LWIR image data 324.

Each of the UMMs 311, 312, 314 is arranged to provide user data indicative of one or more of biometric, physical or psychological attributes of the user to at least one inference module 331, 332, 333, 334. In some embodiments, such as shown in FIG. 3, two or more inference modules 332, 333 may receive the same user data 322. In the illustrated embodiment, the system 300 comprises four inference modules although it will be appreciated that this is merely illustrative.

Each of the inference modules 331, 332, 333, 334 is arranged to determine, or infer, a respective inference of a cognitive state of the user of the vehicle 200. Each of the inference modules 331, 332, 333, 334 is arranged to output user state data indicative of the determined inference of the cognitive state of the user. The cognitive state of the user reflects a state of mind of the user. Each inference module may determine the inference of the cognitive state of the user as one of a plurality of predetermine types of cognitive state which the respective inference module is arranged to determine or detect.

In the embodiment shown in FIG. 3, the four inference modules comprise a biometric inference module 331, an emotion inference module 332, a visual inference module 333, and a thermal inference module 334. It will be appreciated that other embodiments may comprise only some of these modules and may comprise other modules.

The biometric inference module 331 is arranged to infer a biometric-related cognitive state of the user. The biometric inference may be related to biometric attributes of the user such as determinable from the one or more biometric attributes of the user of the vehicle 200, such as the ECG data 321. In one embodiment, the biometric inference module 331 is arranged to determine whether the user has one or both of a stress- or boredom-related cognitive state.

The emotion inference module 332 is arranged to infer a emotive-related cognitive state of the user. The emotion inference may be related to observable attributes of the user such as determinable from the one or more visually-related attributes of the user of the vehicle 200, such as from the user data 322. In one embodiment, the emotion inference module 331 is arranged to determine whether the user has one of a happy, sad, bored, tired, joy, anger, surprise cognitive states, although other states may be envisaged.

The visual inference module 333 is arranged to infer a visually-related cognitive state of the user. The visual inference may be related to observable attributes of the user such as determinable from the one or more visible attributes of the user of the vehicle 200, such as the user data 322. In one embodiment, the visual inference module 333 is arranged to determine whether the user has a bored, annoyed, light-sensitive, tired cognitive state, although other states may be envisaged. The user data 322 in the form of image data may be processed to detect one or more facial features of the user of the vehicle. The facial features may be markers relating to facial features such as smile, eye width, brow position such as raise, furrow etc.

The thermal inference module 334 is arranged to infer a thermally-related cognitive state of the user. The thermal inference may be related to a temperature of at least a portion of the user, such as determinable from the one or more thermal attributes of the user of the vehicle 200, such as the data 324. In one embodiment, the thermal inference module 334 is arranged to determine whether the user cognitive state indicative of being warm, hot, cold etc, although other states may be envisaged.

Figure 4:
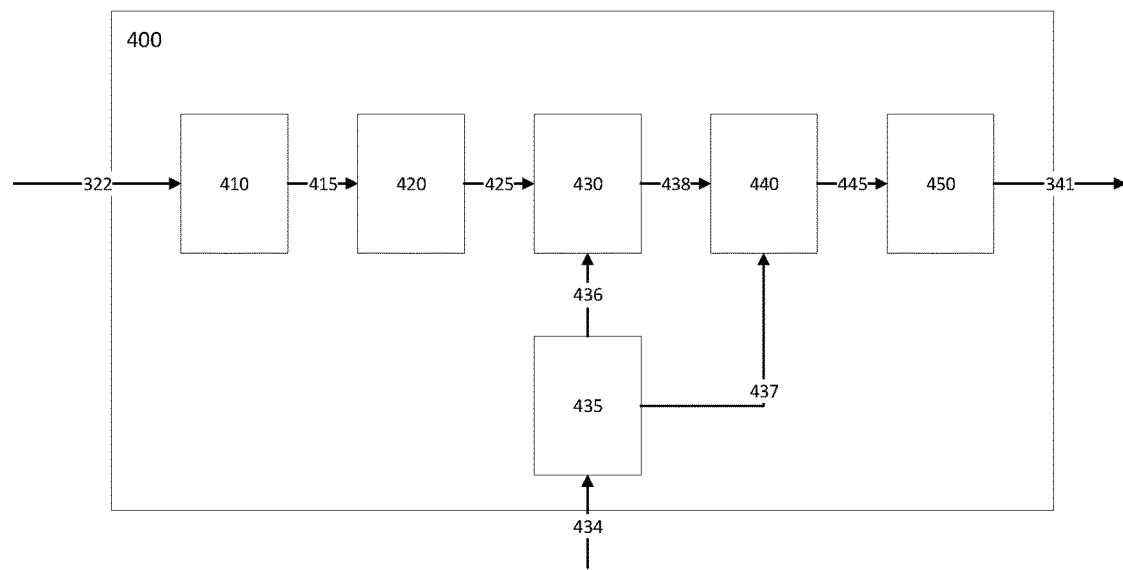
FIG. 4 shows a schematic illustration of an inference module according to an embodiment of the present disclosure.

FIG. 4 schematically illustrates an inference module 400 according to an embodiment of the disclosure. The inference module 400 may correspond to one of the inference modules 331, 332, 333, 334 shown in FIG. 3 and described above. FIG. 4 will be described with reference to the visual inference module 333, although it will be appreciated that other inference modules may adopt the same, or similar, structure.

The inference module 400 comprises an input buffer 410 for buffering received user data 322 to allow processing thereof by the inference module 400 at a different rate than the rate at which the user data is received. The user data 322 may be received in a predetermined data format, such as in the form of messages 322 which may be JSON messages 322, although other formats may be used. Buffered user data 415 is provided from the input buffer 410.

The inference module comprises a data parser 420 for parsing the buffered user data 415. In some embodiments, the data parser 420 is arranged to parse the received messages to extract relevant user data indicative of the state of the user. The parsing may extract data indicative of, for example, a facial feature of the user such as brow furrow or eye closing. The parsed data 425 is provided to a threshold monitor 430.

The threshold monitor 430 is arranged to determine an active state of the user in dependence on the received data 425. The active state of the user is determined by the threshold monitor in dependence on one or more thresholds. Data indicative of the one or more thresholds is provided by a threshold unit 435. The threshold unit 435 may determine the one or more thresholds based on user input 434 received at a user-interface. The threshold unit 435 provides threshold data 436 to the threshold monitor 430, where the threshold data 436 is indicative of an extent or threshold associated with one or more facial features. For example, the threshold data may indicate an extent, or amount, of brow movement (from a normal brow position), to be determined as a significant movement of the brow, for example related to the user being annoyed. A respective threshold may be used for each user feature, such as brow position, eye opening etc. Active state data 438 output by the threshold monitor 430 is indicative of a current active state of the user i.e. substantially at that point in time. Thus the active state data 438 output by the threshold monitor 430 may output an indication, in generally real-time, of the active state of the user.

Figure 5:
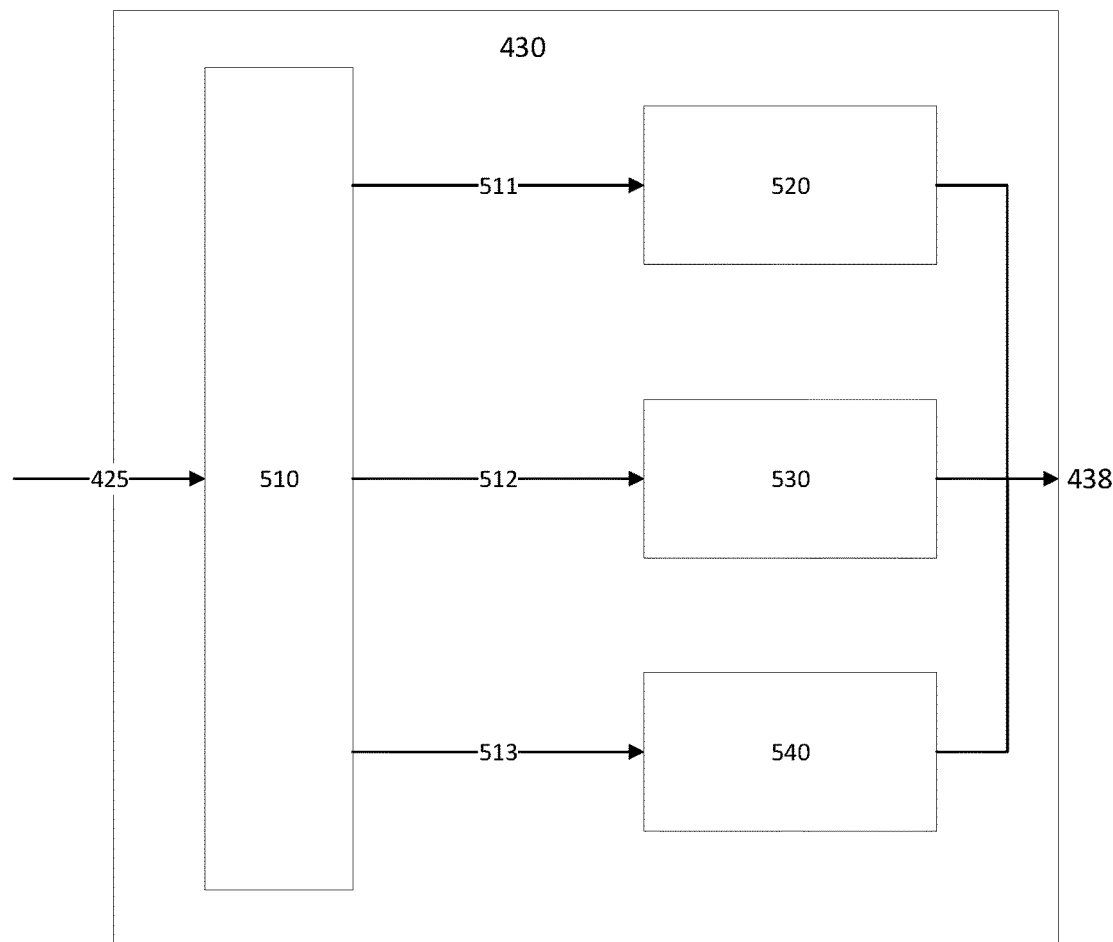
FIG. 5 shows a schematic illustration of a threshold monitor according to an embodiment of the present disclosure.

FIG. 5 further illustrates the threshold monitor 430 according to an embodiment of the disclosure. The illustrated threshold monitor 430 is of the visual inference module 333 although it will be appreciated that others of the inference modules 331, 332, 333, 334 may have a consistent structure.

The threshold monitor 430 comprises a receive data unit 510 and a plurality of monitoring units 520, 530, 540. Each of the monitoring units 520, 530, 540 is arranged to monitor for a respective or specific attribute of the user. For example, in one embodiment, the threshold monitor 430 comprises one or more of a boredom monitoring unit 520, a light annoyance monitoring unit 530 and a tiredness monitoring unit 540. Each of the plurality of monitoring units 520, 530, 540 operates on at least some of the image data 322 received by the visual inference module 333. As described above, the parsing of the received data may extract data indicative of particular facial features of the user such as brow furrow or eye closing. In some embodiments, each of the monitoring units 520, 530, 540 receives data 511, 512, 513 indicative of predetermined facial features. The receive data unit 510 is arranged to distribute the data to the appropriate monitoring unit 520, 530, 540. For example, the boredom monitoring unit 520 is arranged to receive data 511 indicative of the user yawning. The boredom monitoring unit 520 is arranged to determine an inference of the active state of the user being bored in dependence on the data 511 indicative of the user yawning. The light annoyance unit 530 is arranged to receive data 512 indicative of a brow furrow of the user. The light annoyance monitoring unit 530 is arranged to determine an inference of the active state of the user being annoyed by illumination entering or within the vehicle 200 in dependence on the data 512 indicative of the user's brow furrowing. The tiredness monitoring unit 540 is arranged to receive data 513 indicative of one or both of eye closure and a blink rate of the user. The tiredness monitoring unit 540 is arranged to determine an inference of the active state of the user being tired in dependence on the data 513 indicative of the user closing one or both of their eyes, and/or the blink rate of the user of the vehicle 200.

The inference module 400 comprises an active time monitor 440 for inferring the cognitive state of the user. The active time monitor receives the active state data 438 from the threshold monitor 430. The cognitive state is inferred in dependence on the active state of the user and a temporal threshold. The active time monitor 440 is arranged to determine whether the user has adopted an active state for a period of time corresponding to an active time threshold. Data indicative of the active time threshold 437 is provided from the threshold unit 435. If the active state data 438 output from the threshold monitor 430 is indicative of a particular active state of the user, such as the user being annoyed, the active time monitor 440 is arranged to determine if the active state is maintained for at least a duration of time corresponding to the active time threshold 437. If the user state is maintained for the active time threshold, the active time monitor 440 determines the active state of the user, for example the user being annoyed or bored etc. The active time monitor 440 is arranged to output an indication 445 of the inferred cognitive state of the user.

The inference module comprises a data wrapper 450. The data wrapper 450 is arranged to receive the indication 445 of the inferred cognitive state of the user from the active time monitor 440. The data wrapper 450 may, in some embodiments, receive a plurality of inferences of the cognitive state of the user at each of a plurality of points in time. The data wrapper 450 comprises user state data indicative of the inference of the cognitive state of the user at the plurality of points in time. Thus the data wrapper 450 combines or wraps a number of the inferences of the cognitive state of the user and provides a wrapper 341 comprising the plurality of inferences.

In the embodiment shown in FIG. 3, the four inference modules output, respectively, biometric user state data 341, emotion user state data 342, visual user state data 343, and thermal user state data 344. The user state data 341, 342, 343, 344 is received by the inference fusion module 350. In some embodiments, the inference fusion module 350 may also receive user data 321, 322, 324 from one or more of the UMMs 311, 312, 314, such as in one embodiment the second user data 322 in the form of image data of the user.

Figure 6:
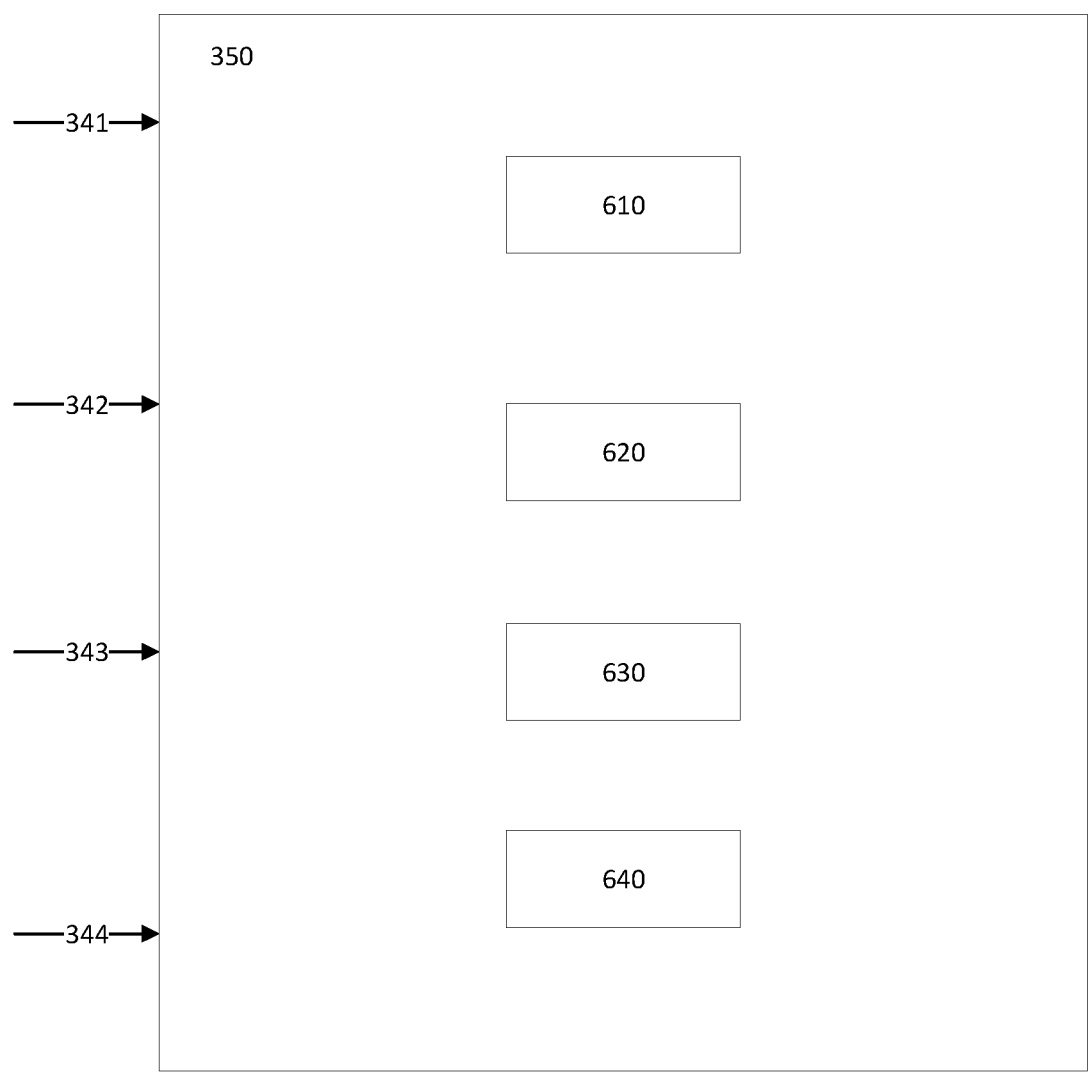
FIG. 6 shows a schematic illustration of an inference fusion module according to an embodiment of the present disclosure.

FIG. 6 illustrates an inference fusion module (IFM) 350 according to an embodiment of the disclosure. The inference fusion module 350 comprises a ground truth unit 610, a baseline parameters (BP) unit 620, a relative baseline parameter offset (RBPO) unit 630 and a learned inference output (LIO) unit 640.

The ground truth unit 610 is arranged to receive or read user state data 341, 342, 343, 344. The ground truth unit 610 uses the user state data 341, 342, 343, 344 as training data for the respective user to enable a ground truth for the user to be determined based on observed user state data. Each user of the vehicle 200 may be recognised and associated with respective data by the IFM 350. Thus, for each user, respective ground truth data is stored in some embodiments in the ground truth unit 610. The ground truth is determined based on the received user state data 341, 342, 343, 344 for each occupant. That is, respective ground truth may be stored for each of a plurality of individual users of the vehicle 200.

As described above, the IFM 350 receives the user state data 341, 342, 343, 344 from the plurality of inference modules 331, 332, 333, 334. The inference fusion module 350 is arranged to determine an inference of an aggregated cognitive state of the user in dependence thereon. The aggregated cognitive state is an aggregation or combination of the inferences of the cognitive state of the user of the vehicle 200 determined by the plurality of inference modules 331, 332, 333, 334. The inference fusion module 350 adaptively determines the cognitive state of the user of the vehicle 200 by learning about the user's normal cognitive state, as will be explained.

The baseline parameters unit 620 is arranged to store data indicative of a baseline or normal cognitive state of the user of the vehicle 200. The baseline parameters unit 620 may adaptively update the data indicative of the baseline cognitive state. The baseline cognitive state is a dormant cognitive state of the user of the vehicle 200. The inference fusion module 350 updates the baseline cognitive state of the user in dependence on received user state data. The inference fusion module 350 may determine a predominant cognitive state of the user over a period of time, for example 10, 20 or 30 minutes although other periods of time may be used. The baseline parameters unit 620 adds data indicative of the predominant cognitive state to the stored user state data such that the baseline cognitive state is dynamically updated. The BP unit 620 may determine the baseline as an average of the user state data 341, 342, 343, 344. The average may be determined over a predetermined period of time. The average may be a rolling average i.e. determined over a time window preceding a current period of time. In this way, the baseline cognitive state may be continually updated.

The RBPO unit 630 is arranged to remove a relative baseline cognitive state from the received user state data (or vice versa). As discussed above, the BP unit 620 stores data indicative of the baseline cognitive state of the user. The RBPO is 630 is arranged to remove, i.e. to subtract, the baseline cognitive state from the received user state data 341, 342, 343, 344 (or vice versa) such that a differential cognitive state of the user is determined. Thus the RBPO unit 630 extracts any offset cognitive state from the baseline in the received user state data 341, 342, 343, 344. That is, at a given point in time, the RBPO is arranged to provide a baseline offset of the user state data 341, 342, 343, 344 for the user of the vehicle 200.

The LIO unit 640 is arranged to determine a correlation between the user state data 341, 342, 343, 344 received by the IFM 350 and each of a plurality of cognitive states of the user. The LIO is updated by the IFM 350 over time, such that the LIO unit 640 stores LIO data indicative of the user state data and the plurality of cognitive states of the user which is updated over the period of time. Effectively the LIO data provides a personalised classifier or inference model for each user of the vehicle 200 which is continually updated in some embodiments. The LIO unit 640 is arranged to label instances of the user data 341, 342, 343, 344 when significant i.e. indicative of a significant cognitive state of the user of the vehicle 200.

Figure 7:
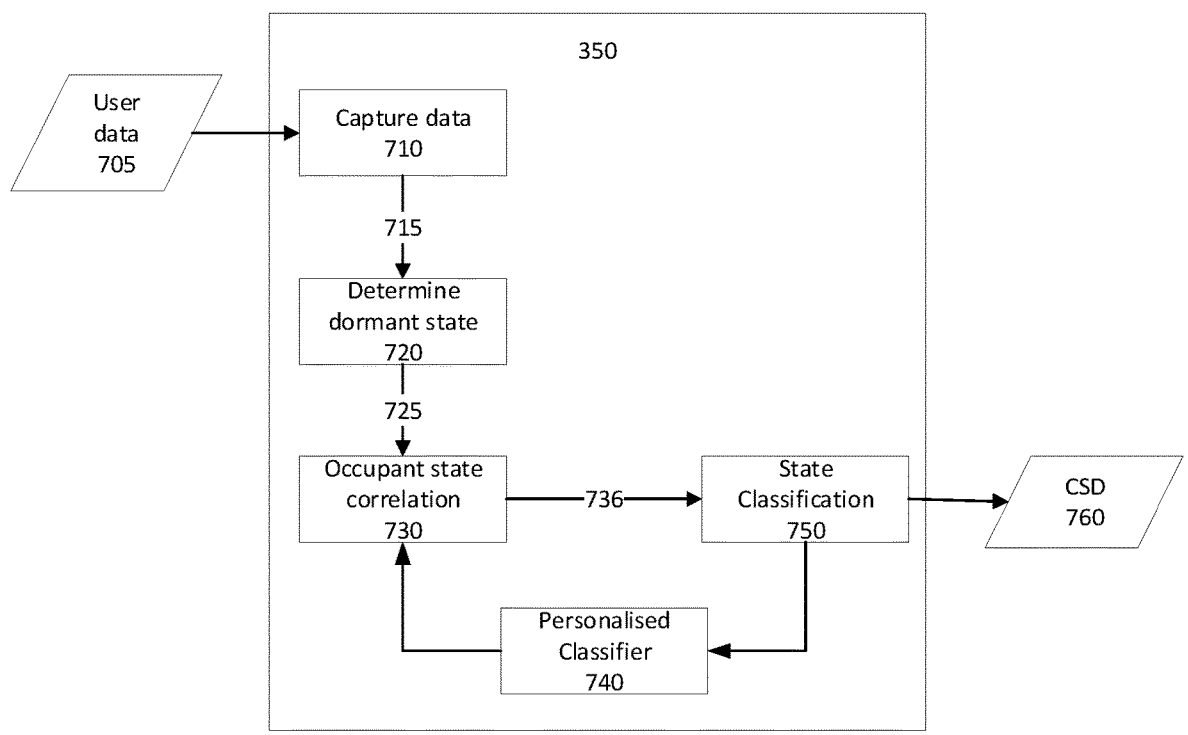
FIG. 7 is a functional diagram of the inference fusion module according to an embodiment of the present disclosure.

FIG. 7 illustrates functional operation of the IFM 350 according to an embodiment of the disclosure. As explained above, the IFM 350 is arranged to receive user state data 341, 342, 343 and may in some embodiments receive user data 321, 322, 324 as indicated in FIG. 7 as user data 705.

In functional block 710 the user data 705 is received by the IFM 350. The received data may be stored, at least temporarily, in order to aid processing by the IFM 350. For example the user data 705 may be buffered in some embodiments. In one embodiment, the user state data 341, 342, 343 is stored and associated with the user data 321, 322, 324. For example, the user state data 341, 342, 343 indicative of the determined inference of the cognitive state of the user may be associated with image data 322 relating to the user at a time of the inference of the cognitive state. This enables the IFM 350 to reference the image data 322 to the inference of the cognitive state of the user at any point in time. The captured user data 715 is provided to functional block 720 to determine a dormant state of the user of the vehicle 200.

In block 720 the dormant (baseline) state of the user is determined and used to normalise the captured user data 715. The dormant state of the user is intended to provide a baseline for each particular user of the vehicle 200. The dormant state is typically the user's natural or resting state, such that received user data 705 may be referenced against the dormant state in order to obtain normalised data. The dormant state may be represented by dormant state data stored to be accessible by the IFM 350.

The dormant state data may be derived from captured user data 715 accumulated over a period of time and used to define, for example, average data values for each type of user data and/or user state data over one or more defined periods of time. For example captured user data representative of a user's heart rate may be used to determine the average heart rate over a period of time for the user. This average heart rate may then be used as dormant heart rate state data. The dormant heart rate state data for the user may then be subtracted from captured heart rate data for the user to obtain normalised heart rate data representative of variances in the user's captured heart rate relative to their dormant heart rate state.

In some embodiments, the average data values for each type of user data and/or user state data may be calculated based on data accumulated over a period of time sufficient to enable a current dormant state of the user to be determined. For example, in a scenario where the user has not performed any significant physical exertion for a long period of time, their heart rate will typically be at a resting heart rate for that user, for example between 60 to 100 bpm. However, if the user has recently performed significant physical exertion, for example has recently been running, their heart rate will typically be elevated, i.e. will typically be at a relatively consistent rate over 100 bpm. Accordingly, in order to take into consideration such variation in the dormant state for certain types of user data the average data value for a type of user data and/or user state data may be calculated based on data accumulated over a period of time of several minutes, for example between 1 to 5 minutes. However, for different types of user data, the average data values may be calculated based on data accumulated over different periods of time, for example longer periods of time where the data is less likely to vary over a short period of time for a particular user but may vary for different users.

An output of block 720 may thus be referred to as normalised state data 725 which is determined by comparing the data indicative of the dormant state of the user against the captured user data 715.

In block 730, correlation of the normalised state data 725 to one or more occupant state models is performed to derive likelihood data 736 indicative of a current likelihood of the user being in one or more cognitive states. The correlation in block 730 may determine an indication of an associated probability or metric for each cognitive state. The associated probability is indicative of a degree of confidence of the correlation.

In some embodiments, the user may be provided with one or more simulated scenarios to prompt or induce normalised state data 725 for the user corresponding to simulated scenario(s) such that the user's responses to such scenarios may be identified to train the occupant state models for that user in order to improve the degree of confidence of the correlation and thus of the likelihood data 736 output thereby.

In block 750, the likelihood data 736 indicative of a current likelihood of the user being in one or more cognitive states is used to generate cognitive state data (CSD) 760 for the user, for example an indication for each cognitive state of whether the user is in such a cognitive state or not.

For example, the likelihood data 736 indicative of a current likelihood of the user being in one or more cognitive states may comprise a metric for each cognitive state. The user may be deemed to be in a particular cognitive state when the respective metric within the likelihood data 736 exceeds a threshold for that cognitive state for longer than a minimum period of time. In this manner, noise and false positives in the likelihood data 736 may be filtered out by requiring the metric to exceed the threshold for at least the minimum period of time before determining the user to be in such a cognitive state. Similarly, the user may be deemed to no longer be in a particular cognitive state when the respective metric within the likelihood data 736 no longer exceeds the threshold for that cognitive state for longer than the, or a, minimum period of time.

In the illustrated embodiment, state classification data derived in block 750 is fed back to block 740, and used to generate historic personalised state classification data for the user. The historic personalised state classification data is then fed back to block 730, where it is used to update the occupant states models to which the normalised state data 725 is correlated. In this manner, the historic personalised state classification data is used to train and refine the correlation models for each user, and thereby further improve over time the degree of confidence of the correlation and thus of the probability or metric values 736 output.

Figure 8:
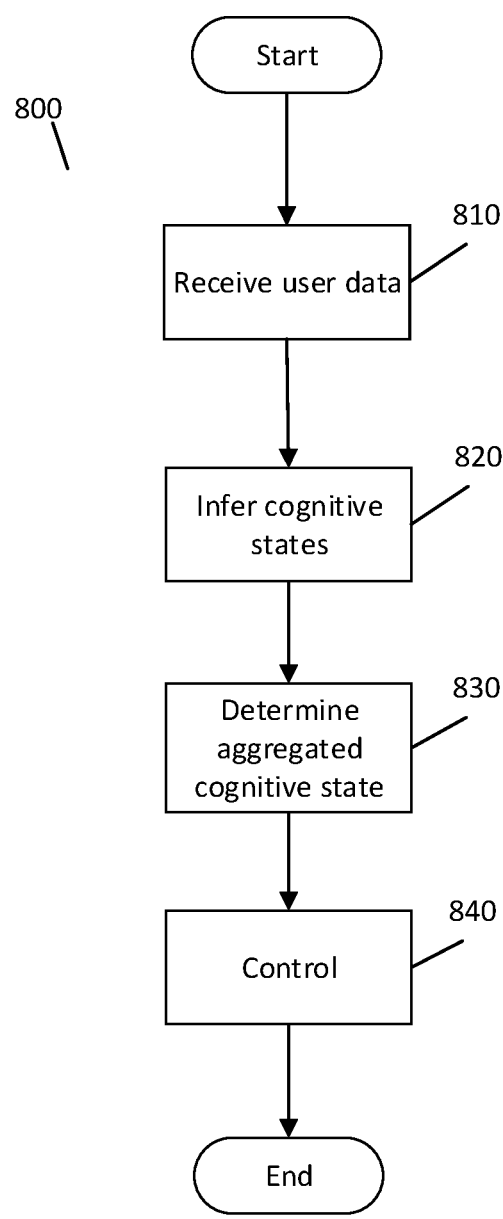
FIG. 8 illustrates a method according to an embodiment of the present disclosure.

FIG. 8 illustrates a method 800 according to an embodiment of the disclosure. The method 800 may be performed by the system 300 described above particularly with reference to FIGS. 3-7. The method 800 is a method of determining a cognitive state of the user of the vehicle 200. The method 800 may be performed to control one or more functions of the vehicle 200 dependent on the cognitive state of the user, as will be explained.

The method 800 comprises, at 810, receiving user data 321, 322, 324 indicative of respective attributes of the user of the vehicle 200 from the one or more UMMs 311, 312, 314. As described above, the user data 321, 322, 324 may be indicative of biometric, physical and psychological attributes of the user of the vehicle 200. The user data 321, 322, 324 is received at the plurality of inference modules 331, 332, 333, 334, as described above. 810 may comprise receiving the context data 145 from the mobile device 10 as also described above.

The method 800 further comprises, at 820, determining an inference of one or more cognitive states of the user in dependence on the user data 321, 322, 324. The inference of the one or more cognitive states of the user may be determined as described above in connection with FIGS. 4 and 5 in particular.

The determination of the inference of the one or more cognitive states at 820 may comprise receiving the user data 321, 322, 324 and one more threshold values. In dependence on the user data and at least one threshold value, a determination is made of an active state of the user as described above. In some embodiments, 820 comprises receiving an indication of a temporal threshold value. 820 further comprises determining, in dependence on the received temporal threshold value, the inference of the cognitive state of the user.

At 830 an inference of an aggregated cognitive state of the user is determined. The inference of the aggregated cognitive state may be determined in the form of the cognitive state data 760 as described above with reference to FIG. 7 in particular.

The inference indicative of the aggregated cognitive state is utilised at 840 for controlling one or more functions of the vehicle 200. For example, the one or more functions may include controlling one or more aspects of an interior of the vehicle, such as temperature, luminance, an output of an audio-visual system of the vehicle 200, a navigation system of the vehicle. It will be appreciated that other functions of the vehicle may also be controlled, such as a suspension system of the vehicle i.e. to control a ride characteristic of the vehicle, a power unit of the vehicle or a drivetrain of the vehicle 200 to control one or more driving characteristics of the vehicle. The control of one or more functions of the vehicle 200 will be described in more detail below.

According to some embodiments of the disclosure there is provided a system 900 for controlling one or more functions of the vehicle responsive to a cognitive state of the user. The system 900 comprises a response engine 360 for controlling one or more functions of the vehicle 200. The response engine 360 may be implemented by the hardware of the system 100 described with reference to FIG. 1.

Figure 9:
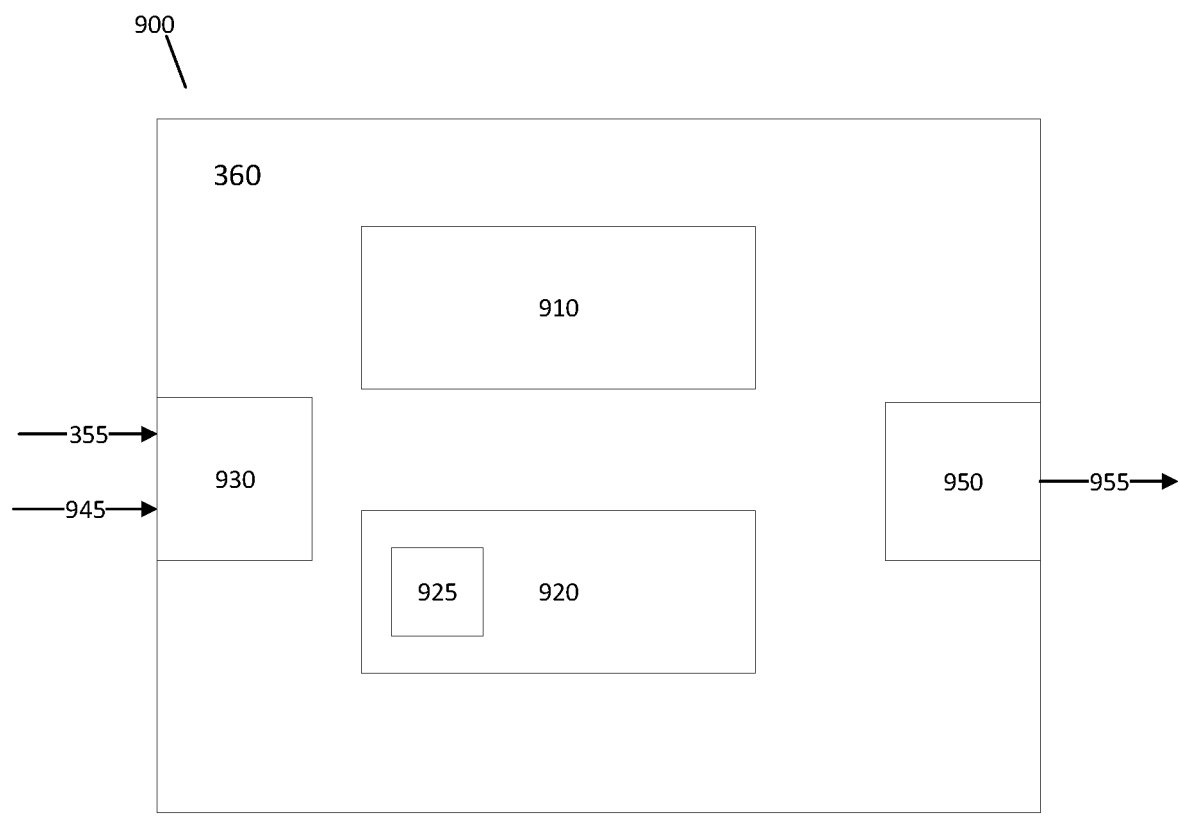
FIG. 9 shows a schematic illustration of a response engine according to an embodiment of the present disclosure.

FIG. 9 schematically illustrates a response engine 360 according to an embodiment of the disclosure.

The response engine 360 comprises input means 930 to receive data. The input means 930 may comprise one or more electrical inputs 115 to the controller 110 on which the response engine 360 is implemented. The input means 930 is configured to receive cognitive state data 355, 760 indicative of a cognitive state of a user of the vehicle. In some embodiments, the cognitive state data 355, 760 may be received by the response engine 360 from the inference fusion module 350. The cognitive state may, in some embodiments be the aggregated cognitive state of the user determined by the method 800.

The cognitive state data 355, 760 may be indicative of an attentiveness of the user to a current task. For example, the cognitive state data 355, 760 may be indicative of a level of boredom or tiredness of the user, although it will be appreciated that any cognitive state of the user may be indicated, in particular those described with reference to the output of the inference fusion module (IFM) 350.

The input means 930 is configured to receive context data 945 indicative of a context of one or both of the user and the vehicle. The context data 945 may comprise one or both of the vehicle data 135 and the user context data 145. For example, the context data 945 may be indicative of an environment of the user in the vehicle, such as one or more of a luminance, audible, thermal or physical environment. The environment of the user may be associated with one or more adjustable settings for configuring aspects of the environment, which may be controlled by control data 955 output from the response engine 360, as will be explained.

The context data 945 may in some embodiments be indicative of a geographic location of the vehicle, for example in the form of navigation data such as GLONASS or GPS data.

In some embodiments the context data 945 may be indicative of a status of the user in the vehicle, as has been described with reference to the user context data 145. For example, the context data 945 may be indicative of one or more of an activity being undertaken by a user or a location of the user within the vehicle. For example the context data 945 may indicate that the user is driving, and located in a driver seat of the vehicle, although it will be appreciate that the disclosure is not limited to being implemented for any particular status or set of statuses of the user.

The response engine 360 comprises a data storage module 920 which may be implemented on the one or more memory devices 112 of the system 100. The data storage module is configured to store preference data 925 indicative of one or more preferences associated with the user. In some embodiments, the preferences associate one or more of the cognitive states of the user with one or more settings of at least one vehicle system. Optionally the preferences may further associate the context of the user and/or vehicle with one or more settings of the at least one vehicle system. In some embodiments, the preferences associate one or more cognitive states of the user in at least one context with one or more media content preferences.

The response engine 360 comprises a decision module 910, which may be implemented by computer-readable software instructions stored on a computer readable medium, such as the one or more memory devices 112 of the system 100, and may be executed on the one or more electronic processors 111 of the system 100. The decision module 910 is configured to determine control data 955 for controlling one or more functions of the vehicle. The decision module 910 may be configured to determine the control data 955 in dependence on the cognitive state data 355, the preference data 925 and the context data 945.

In some embodiments, the one or more functions of the vehicle may relate to the environment of the user of the vehicle. The decision module 910 may be configured to determine the control data 955 for controlling one or more aspects of the environment of the vehicle. For example, for controlling one or more heating, ventilation or air-conditioning (HVAC) settings associated with the vehicle, or one or more settings associated with an audio environment within a vehicle, for example a volume of media output in the vehicle.

In some embodiments, the one or more functions of the vehicle may comprise a navigation system of the vehicle, and the control data 955 may comprise navigation data for controlling the navigation system. For example, the decision module 910 may determine control data 955 for amending or setting a route for the navigation system of the vehicle.

In some embodiments, the one or more functions of the vehicle may comprise a powertrain or suspension system of the vehicle, and the control data 955 may comprise an indication of one or more settings associated with the powertrain or suspension system. For example, the decision module 910 may determine control data 955 for amending a setting of the powertrain or suspension system to affect a comfort level or experience of the user of the vehicle, such as a setting for a driving mode of the vehicle.

The decision module 910 may be configured to learn user preferences and iteratively update the preference data 925 stored in the data storage module 920. The decision module 910 may learn user preferences as it receives cognitive state data 355 and context data 945, as will be explained. In some embodiments the decision module 910 may receive further cognitive state data after outputting control data The response engine 360 comprises output means 950 for outputting the control data 955 for controlling the one or more functions of the vehicle. The output means 950 may comprise one or more electrical outputs 116 to the controller 110.

Figure 10:
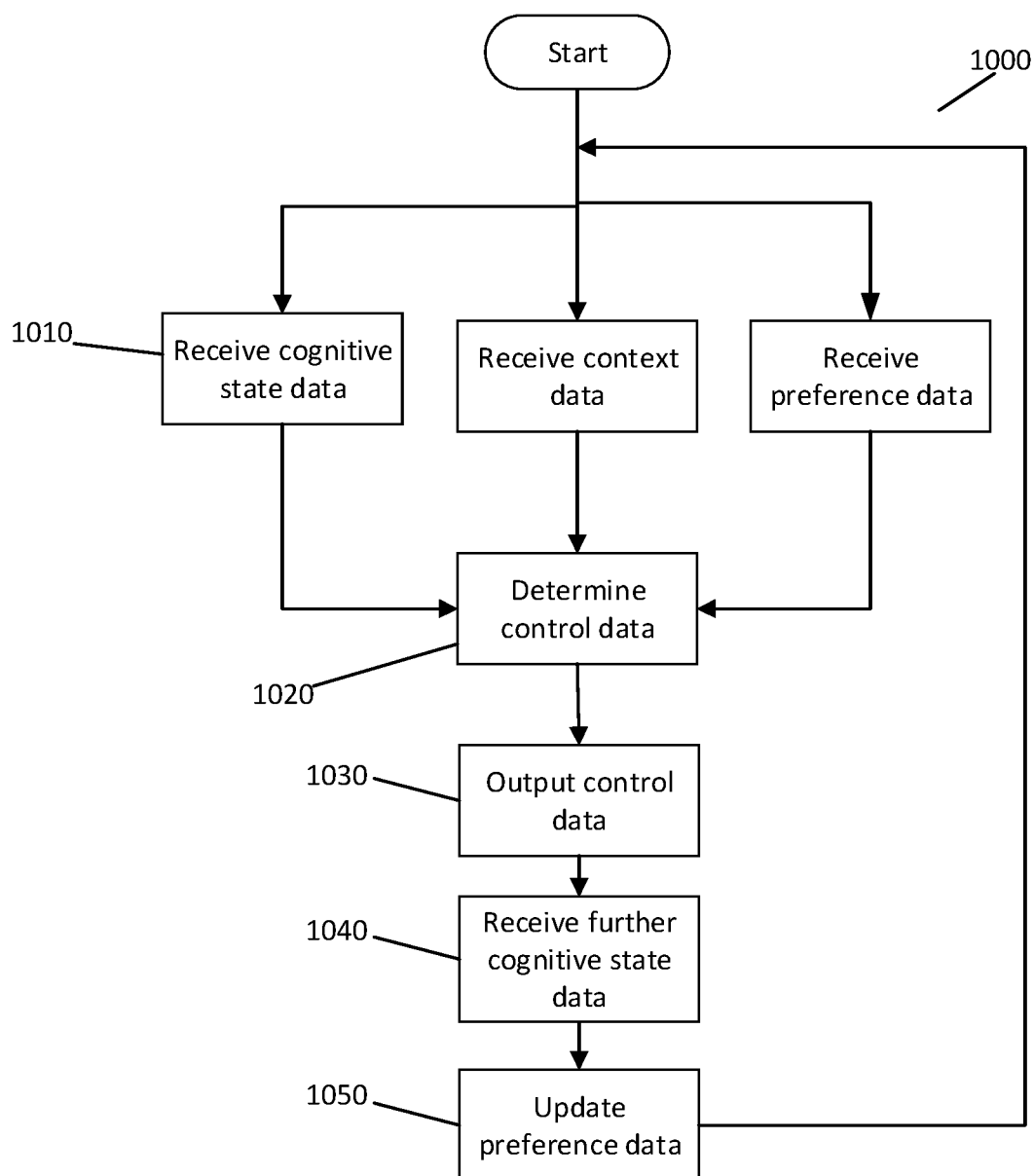
FIG. 10 shows a method according to an embodiment of the present disclosure.

FIG. 10 illustrates a method 1000 according to an embodiment of the disclosure. The method 1000 may be performed by the system 300 or 900. In particular the method 1000 may be performed by the response engine 360 described above with reference to FIG. 9. The method 1000 is a method for controlling one or more functions of the vehicle 200 dependent on the cognitive state of the user, as will be explained.

The method 1000 comprises, at 1010, receiving cognitive state data 355, context data 945 and preference data 925 each of which have been described above. 1010 may comprise receiving one or both of the cognitive state data 355 and context data 945 via the input means 930, and accessing the preference data 925 from the data storage module 920, although it will be appreciated that any or all of the data received at 1010 may be received via the input means, or may be accessed from storage such as data storage module 920. 1010 may comprise receiving each of the cognitive state data 355, context date 945 and preference data 925 concurrently or non-concurrently.

The method 1000 comprises, at 1020, determining control data 955. The control data 955 may be determined by the decision module 910 for controlling one or more functions of the vehicle. The control data 955 may be determined in dependence on the cognitive state data 355, the preference data 925 and the context data 945 as has been explained.

The control data 955 may be determined to control one or more functions of the vehicle to align with the user preferences indicated by the preference data 925. As described, the preferences may associate one or more of the cognitive states of the user with one or more settings of at least one vehicle system. The preferences may associate one or more cognitive states of the user with settings which serve to improve or otherwise alter the one or more cognitive states. The decision module 910 may at step 1020 determine the control data 955 to change the one or more settings of the vehicle system associated with the current cognitive state of the user. For example, the cognitive state data 355 may indicate the user is in a tired or inattentive cognitive state. The preference data 925 may associate a tired cognitive state with a reduction in temperature to reduce the tiredness of the user. The decision module 910 may determine the control data 955 for implementing a reduced temperature setting for the HVAC system of the vehicle.

In another example, the preference data 925 may associate a cognitive state of the user with one or more media content preferences. For example, the preference data 925 may associate a bored cognitive state of the user with a type of media content, e.g. jazz music, and consequently settings for a media system of the vehicle to implement playback of the type of media content. The decision module 910 may then determine the control data 955 for adjusting the settings of the media system to play the type of media content.

The preference data 925 may associate a cognitive state of the user with different settings in dependence on the context data 954. The preference data 925 may associate a cognitive state with a first setting given a first context of the user, and a second setting given a second context of the user. For example, the preference data 925 may associate for the user a bored cognitive state with a first type of media content if the user is driving, and a second type of media content if the user is not driving. The decision module 910 may determine the control data 955 further in dependence on the context data 945 and the user preference for the context indicated. For example, if the context data 945 indicates that the user is driving, and the cognitive state data 355 indicates the user is bored, the decision module 910 may determine the control data 955 for controlling the function of the media system of the vehicle to play back the first type of media content.

The method 1000 comprises, at 1030, outputting the control data 955. The control data 955 may be communicated to each relevant vehicle system for controlling the one or more functions of the vehicle determined at 1020.

The method 1000 comprises, at 1040, receiving further cognitive state data 355 responsive to the control of the one or more vehicle functions. The further cognitive state data 355 may be indicative of the cognitive state of the user subsequent to the control of the one or more functions of the vehicle. The further cognitive state data 355 may be indicative of the cognitive state of the user a predetermined time subsequent to the control of the one or more functions of the vehicle.

The method 1000 comprises, at 1050, updating the preference data in dependence on the further cognitive state data. The decision module 910 may learn user preferences by receiving further cognitive state data responsive to controlling vehicle functions, as has been explained. The decision module 910 may iteratively update the preference data 925 stored in the data storage module 920 responsive to the learned preferences. The decision module 910 may update the preference data indicative of a correlation between the cognitive state and the control of the one of more functions of the vehicle. That is, the preference data may be updated to reflect any effect of the control of the one or more vehicle functions by the control data 925 on the cognitive state of the user. In particular, the decision module 910 may update the preference data 925 to indicate a positive correlation between the further cognitive state and the settings of the vehicle system controlled by the control data 955. If the settings correlate with an improvement in the cognitive state of the user, the decision module may determine a user preference for the settings and update the preference data 925 responsively.

Conversely, the preference data 925 may already indicate an association between a cognitive state and a setting of a vehicle system. If the cognitive state of the user is not improved by controlling the vehicle system to the indicated setting, the decision module 910 may update the preference data 925 to remove or amend the indicated setting as a user preference.

The method 1000 may be performed iteratively by the response engine 360 to update the user preferences in the preference data 925 and consequently better tailor the output control data 955. Associations between cognitive state, context and one or more vehicle settings may be repeatedly updated as the one or more vehicle functions are controlled by the response engine 360. Further control data 955 may then be output during further iterations of the method 1000 in dependence on the updated preference data 925, and the current context and cognitive state of the user. In this way, the method 1000 may adaptively learn user preferences and tailor the control of vehicle systems responsively.

It will be appreciated that embodiments of the present disclosure can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present disclosure. Accordingly, embodiments provide a program comprising code for implementing a system or method and a machine readable storage storing such a program. Still further, embodiments of the present disclosure may be conveyed electronically via any medium such as a communication signal carried over a wired or wireless connection and embodiments suitably encompass the same.

All of the features disclosed in this specification (including any accompanying embodiments), and/or all of the steps of any method or process so disclosed, may be combined in any combination, except combinations where at least some of such features and/or steps are mutually exclusive.

Each feature disclosed in this specification (including any accompanying embodiments), may be replaced by alternative features serving the same, equivalent or similar purpose, unless expressly stated otherwise. Thus, unless expressly stated otherwise, each feature disclosed is one example only of a generic series of equivalent or similar features.

The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A system for determining a cognitive state of a user of a vehicle to control one or more functions of the vehicle, the system being implemented by one or more controllers, the system comprising:
   one or more inputs for receiving user data from a plurality of associated user monitoring devices for each monitoring at least one respective attribute of the user of the vehicle, the user data being indicative of the plurality of respective attributes;
   one or more electronic processors configured to execute a plurality of inference modules and an inference fusion module, wherein:
      the plurality of inference modules is each arranged to receive user data from one or more of the user monitoring devices, and to each determine a respective inference of a cognitive state of the user based at least in part on the received user data, wherein each of the plurality of inference modules is arranged to output user state data indicative of the determined inference of the cognitive state of the user; and
      the inference fusion module is arranged to receive the user state data from each of the plurality of inference modules, to determine an inference of an aggregated cognitive state of the user and to output cognitive state data indicative of the aggregated cognitive state for controlling the one or more functions of the vehicle based thereon, the inference fusion module being further configured to determine, in dependence on the received user state data from each of the plurality of inference modules, likelihood data indicative of a current likelihood of the user being in one or more cognitive states, and determine the inference of the aggregated cognitive state based at least in part on whether the likelihood data exceeds a threshold for that cognitive state for longer than a minimum period of time; and
   an output configured to output control data for controlling the one of more functions of the vehicle, the control data generated based on the cognitive state data.

2. The system of claim 1, wherein the each of the plurality of inference modules are arranged to output a wrapper including user state data indicative of the determined inference of the cognitive state of the user at a plurality of points in time.

3. The system of claim 1, wherein the inference fusion module is arranged to determine the aggregated cognitive state of the user based at least in part on the received user state data and one or more baseline parameters associated with the user indicative of a dormant state of the user.

4. The system of claim 3, wherein the inference fusion module is arranged to update the one or more baseline parameters associated with the user based at least in part on the user data.

5. The system of claim 1, wherein the inference fusion module is arranged to determine the aggregated cognitive state of the user based at least in part on the received user state data and learned inference information associated with the user, wherein the learned inference information associates user data with one or more cognitive states.

6. The system of claim 1, wherein the inference fusion module comprises relative baseline offset (RBO) information and the inference fusion module is arranged to process the user state data based at least in part on the RBO information to remove an offset from the user data.

7. The system of claim 1, wherein:
   the one or more inputs is configured to receive context data indicative of a context of one or both of the user and the vehicle; and preference data indicative of one or more preferences associated with the user, where the one or more preferences associate one or more of the cognitive states of the user with one or more settings of at least one vehicle system; and wherein the system further comprises:
   one or more electronic processors for controlling the one or more functions of the vehicle based on the control data, wherein the control data is generated based at least in part on the cognitive state data, the context data and the preference data;
   wherein the one or more electronic processors is arranged to receive further cognitive state data responsive to the control of the one or more functions of the vehicle, wherein the one or more electronic processors is arranged to update the preference data indicative of a correlation between the cognitive state and the control of the one of more functions of the vehicle.

8. The system of claim 1, wherein:
   the one or more inputs is arranged to receive visual user data from a visual monitoring device for visually monitoring the user of the vehicle;
   the plurality of inference modules comprise a visual inference module arranged to determine an inference of a visual state of the user based at least in part on the visual user data and to output visual state data indicative of the inference of the visual state of the user.

9. The system of claim 8, wherein the visual user data is facial expression data indicative of one or more attributes of a facial expression of the user.

10. The system of claim 9, wherein the visual inference module comprises a plurality of visual state monitoring units, wherein each monitoring unit is arranged to identify a respective visual state of the user.

11. The system of claim 1, wherein:
   the one or more inputs comprise an input for receiving biometric user data from a biometric monitoring device for monitoring one or more biometric attributes of the user of the vehicle;
   the plurality of inference modules comprise a biometric inference module arranged determine an inference of a biometric state of the user based at least in part on the biometric user data, and to output the user state data indicative of the inference of the biometric state of the user.

12. The system of claim 11, wherein the biometric user data is indicative of one or more of a heart rate or skin conductance value of the user.

13. The system of claim 1, wherein:
   the one or more inputs comprise an input for receiving thermal user data from a temperature monitoring device for monitoring a temperature of at least a portion of the user of the vehicle;
   the plurality of inference modules comprise a thermal inference module arranged determine an inference of a thermal state of the user based at least in part on the thermal user data, and to output thermal state data indicative of the inference of the thermal state of the user.

14. The system of claim 1 wherein:
   the one or more inputs comprise an input for receiving gaze data from a gaze monitoring device for monitoring a gaze of the user of the vehicle;

the plurality of inference modules comprise a gaze inference module arranged determine an inference of a gazing state of the user based at least in part on the gaze data, and to output gaze state data indicative of an inference of a visual state of the user.

15. The system of claim 1, wherein the one or more inputs comprise an input means for receiving contextual user data from a device associated with the user, wherein the contextual user data is indicative of a behavior of the user prior to entering the vehicle.

16. The system according to claim 1 comprised in the vehicle.

17. The system of claim 1, wherein one or more of the plurality of inference modules comprises:
   a threshold monitor arranged to receive the user data and to determine, based at least in part on the user data and at least one threshold value, an active state of the user; and
   an active time monitor arranged to receive an indication of the active state from the threshold monitor and to determine, based at least in part on a temporal threshold value, the inference of the cognitive state of the user.

18. The system of claim 1, wherein the inference fusion module comprises relative baseline offset (RBO) information, wherein the inference fusion module is arranged to process the user state data based at least in part on the RBO information to remove a baseline cognitive state from the user state data to form normalized user state data, wherein the inference fusion module is configured to determine the inference of the aggregated cognitive state of the user based on the normalized user state data, and wherein the baseline cognitive data is determined as an average of prior user state data received over a predetermined period of time.

19. A non-transitory, computer-readable storage medium storing instructions thereon that, when executed by one or more electronic processors, causes the one or more electronic processors to carry out a method of determining a cognitive state of a user of a vehicle to control one or more functions of the vehicle, the method comprising:
   receiving user data from a plurality of associated user monitoring devices for each monitoring at least one respective attribute of the user of the vehicle, the user data being indicative of the plurality of respective attributes;
   using a plurality of inference modules to determine a plurality of inferences of respective cognitive states of the user based at least in part on the received user data;
   determining, with an inference infusion module, an inference of an aggregated cognitive state of the user indicative of the aggregated cognitive state for controlling the one or more functions of the vehicle based thereon, the inference fusion module being further configured to determine, in dependence on the plurality of inferences of respective cognitive states of the user, likelihood data indicative of a current likelihood of the user being in one or more cognitive states, determine the inference of the aggregated cognitive state based at least in part on whether the likelihood data exceeds a threshold for that cognitive state for longer than a minimum period of time, and output cognitive state data indicative of the aggregated cognitive state; and
   outputting control data for controlling the one of more functions of the vehicle, the control data generated based on the cognitive state data.

* * * * *